(12) United States Patent
Gavin et al.

(10) Patent No.: US 12,000,817 B2
(45) Date of Patent: Jun. 4, 2024

(54) MILKING SYSTEM WITH SAMPLING DEVICE

(71) Applicant: LELY PATENT N.V., Maassluis (NL)

(72) Inventors: Peter Michael Gavin, Maassluis (NL); Abram Christiaan Knip, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 537 days.

(21) Appl. No.: 17/273,370

(22) PCT Filed: Sep. 19, 2019

(86) PCT No.: PCT/NL2019/050616
§ 371 (c)(1),
(2) Date: Mar. 4, 2021

(87) PCT Pub. No.: WO2020/067878
PCT Pub. Date: Apr. 2, 2020

(65) Prior Publication Data
US 2021/0341447 A1    Nov. 4, 2021

(30) Foreign Application Priority Data
Sep. 24, 2018  (NL) .................................... 2021687

(51) Int. Cl.
*G01N 33/04* (2006.01)
*A01J 5/013* (2006.01)
*G01N 35/00* (2006.01)

(52) U.S. Cl.
CPC ............ *G01N 33/04* (2013.01); *A01J 5/0131* (2013.01); *G01N 35/00009* (2013.01)

(58) Field of Classification Search
None
See application file for complete search history.

(56) References Cited

U.S. PATENT DOCUMENTS 5,096,828 A * 3/1992 Ishizaka ........... G01N 35/00009
422/66
5,120,506 A * 6/1992 Saito ..................... B01L 1/02
422/66
(Continued)

FOREIGN PATENT DOCUMENTS

CN          1225611 A      8/1999
CN        202481798 U    10/2012
(Continued)

OTHER PUBLICATIONS

International Search Report, issued in PCT/NL2019/050616, dated Feb. 13, 2020.
(Continued)

*Primary Examiner* — Brandi N Hopkins
*Assistant Examiner* — Nigel H Plumb
(74) *Attorney, Agent, or Firm* — Birch, Stewart, Kolasch & Birch, LLP

(57) ABSTRACT

A milking system includes a milking device, a milk line for carrying milk, and a sampling unit arranged to take a sample from the milk line and test the sample for the presence or concentration of at least one substance. The sampling unit is provided with a housing. The housing includes a supply reel with a tape that carries reagent, and a sample supplier. The sampling unit includes a tape displacer displacing the tape, a sample analyser, and a used tape collector device collecting tape with reagent to which a sample has been supplied. The supply reel at a surface thereof includes a desiccant, or is completely made of a desiccant material. This provides such a large volume of desiccant that the correspondingly high moisture absorption capacity ensures an uninterrupted useful life of the sampling unit, and thus of the milking system.

19 Claims, 2 Drawing Sheets

(56) References Cited

U.S. PATENT DOCUMENTS

Figure 1:
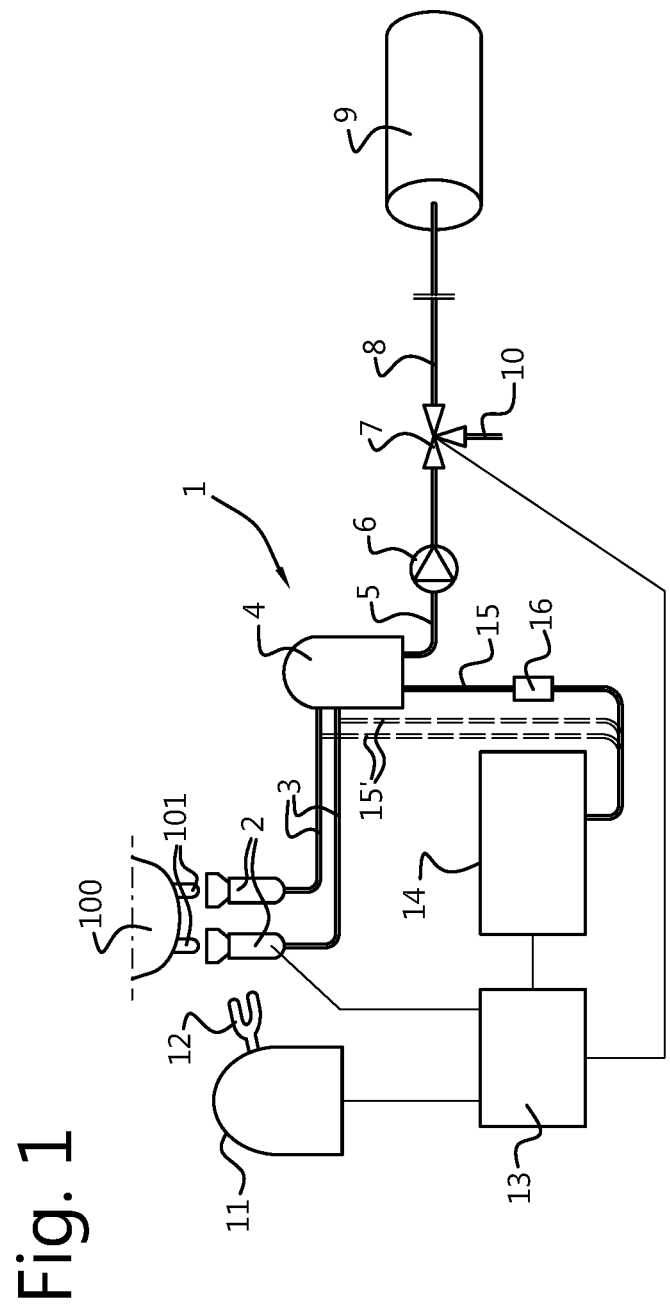

| | | | |
|---|---|---|---|
| 5,911,937 A | 6/1999 | Hekal | |
| 6,130,263 A | 10/2000 | Hekal | |
| 2002/0124803 A1* | 9/2002 | Chen | A01K 1/12 119/14.08 |
| 2005/0232815 A1* | 10/2005 | Ruhl | G01N 33/48764 422/66 |
| 2005/0248864 A1 | 11/2005 | Roe et al. | |
| 2017/0299502 A1 | 10/2017 | Schanzer et al. | |

FOREIGN PATENT DOCUMENTS

| | | |
|---|---|---|
| CN | 104704363 A | 6/2015 |
| EP | 1 381 269 B2 | 5/2014 |
| FR | 3 058 734 A1 | 5/2018 |
| WO | WO02/069697 A1 | 9/2002 |
| WO | WO2005/108960 A1 | 11/2005 |

OTHER PUBLICATIONS

Written Opinion of the International Searching Authority, issued in PCT/NL2019/050616, dated Feb. 13, 2020.

* cited by examiner

MILKING SYSTEM WITH SAMPLING DEVICE

The present invention relates to a milking system, comprising milking means, at least one milk line for carrying milk from the milking means, and a sampling unit that is arranged to take a sample from the milk line and to test the sample for the presence or concentration of at least one substance, wherein the sampling unit is provided with a control unit, a supply reel with a tape that carries reagent, a tape displacer displacing the tape under control of the control unit, a sample supplier to supply, under control of the control unit, at least a part of the sample to the reagent on the tape, and a used tape collector device collecting tape with reagent to which a sample has been supplied.

Such a milking system with a sampling device is known from e.g. EP 1 381 269 B2.

A problem with the known system is that the reagent on the tape is very sensitive to in particular moisture, such as moisture in the air. This moisture is present in high concentrations in the milking barn environment where the system is used, and it may affect the reagent during the useful life of the tape, which may be many days. Although the known system applies a protective sealing tape, this, too, has disadvantages, since the sealing tape presents waste, it requires a mechanism to remove it from the tape with reagent, and it may affect the reagent when being removed from the tape, such as by sticking to part of it.

In addition, the total volume of samples supplied to the tape amounts to a substantial liquid volume. Therefore the requirements for keeping the (relative) humidity sufficiently low.

The present invention has as an object to provide a system of the kind mentioned in the introduction, that has a good resistance against moisture, but that does not, or at least to a lesser extent, have the disadvantages of the known system, or at least presents the public with a useful alternative.

This object is achieved by means of a milking system according to claim 1, in particular a milking system, comprising milking means, at least one milk line for carrying milk from the milking means, and a sampling unit that is arranged to take a sample from the milk line and to test the sample for the presence or concentration of at least one substance, wherein the sampling unit is provided with a control unit and a housing, wherein the housing comprises therein a supply reel with a tape that carries reagent, and a sample supplier to supply, under control of the control unit, at least a part of the sample to the reagent on the tape, the sampling unit further comprising a tape displacer displacing the tape under control of the control unit, a sample analyser, and a used tape collector device collecting tape with reagent to which a sample has been supplied, wherein the supply reel at a surface thereof comprises a desiccant.

Although providing an amount of a desiccant material per se is generally known, cfr. sachets of silicagel in packages and the like, such use is hardly practicable in the present systems and sampling devices, e.g. since providing such materials inside the housing would require a too large housing. This might lead to a too large volume of air that in turn might comprise too much moisture, so that in the end the desiccant material's only job would be to try and demoisturising the air, without any real significance for keeping the moisture away from the reagent. By the present invention, this problem is solved by providing the material at a surface of the supply reel. This surface is present anyway, and thus providing the desiccant material at the surface thereof does not lead to a larger volume of the housing in any way. Furthermore, the desiccant is now extremely close to the reagent, i.e. the material to protect against moisture. Moreover, the surface area that can be provided with the desiccant material, which area is a measure of the desiccating power, is quite large, so the useful life of the housing with the tape with reagent may be made long without additional measures.

In the context of the present invention, the milking means may be conventional milking means, i.e. in which the teat cups are attached manually, or a milking robot, i.e. with automatic teat cup attachment. The milking means collect milk and send it to a bulk storage tank via a milk line, either directly or after temporary storage in a milk jar. The type of milking means or milk line is not relevant for the present invention, and will thus not be given in much detail here.

The sampling unit is arranged to take a (milk) sample from the milk line, in any known way. Herein, "milk line" comprises the complete milk carrying part, from the milk duct connected to a teat cup up to the bulk milk tank, and thus also includes any milk jar of main milk line. The sampling unit may comprise any sensor that is arranged to detect a change in the reagent after a sample of the milk has been supplied thereto. An example thereof is an optical camera. Details of the method of sampling, or of the sensor of the sampling unit are not relevant for the present invention, and are thus given only where needed.

Particular embodiments of the invention are described in the attached dependent claims, as well as in the description that follows.

According to the invention, the supply reel carrying tape with unused reagent is provided in the housing. It is thereby already well protected against moisture from the environment. The housing also comprises a sample supplier therein. This means that at least some structure, such as a nozzle and a tube connected thereto, are present within the housing. Needless to say, the sample supplier may be connected to other parts, and in the end also operably connected to the milk line, these latter parts not being provided in the housing.

Preferably, the used tape collector device is provided in the housing. The used tape, and even the used tape collector device itself, may play a role in improving the moisture characteristics of the sampling unit. The used reagent pads, that are now exposed to the atmosphere within the housing, may continue to absorb moisture. The tape collector device may also have moisture absorption properties, which will be elucidated further below when discussing particular embodiments. Furthermore, the tape displacer may have some connection to the outside world through the housing. In principle these possible channels allow some seeping in of moisture. This can be prevented by means of for example a magnetic coupling.

In embodiments, the supply reel is provided in a subhousing within the housing with an exit opening for the tape. In this embodiment, the supply reel, and thus the reagent on the part of the tape that is still inside the subhousing, is even better protected against moisture from the environment. Not only does the subhousing form itself an additional barrier, but the desiccant at the surface of the supply reel furthermore only needs to remove moisture from the air in the subhousing, which has a smaller volume than the whole housing. This ensures an even longer useful life of the tape with non-used reagent.

Preferably, the exit opening seals onto the tape, in order to protect the subhousing from (moist) air entering the subhousing. Thereto, the subhousing comprises, in embodiments, a duckbill or other flexible seal across the exit opening.

In embodiments, the used tape collector device comprises a collecting reel onto which the tape with the used reagent is collected by the tape displacer. In particular, the used tape collector device also comprises a desiccant at a surface of the collecting reel. In embodiments, the used tape collector device, in particular the collecting reel, is provided directly in the housing.

Herein, "provided directly in" means that the collecting reel is not shielded from the air inside the housing, i.e. it is not placed in a subhousing, thus contrary to the supply reel in some embodiments.

In embodiments, the supply reel is substantially made of desiccant. This is intended to comprise the situation that the supply reel is made of a mixed, or compound, material that contains a pure desiccant and at least one other material, such as a binder, a channeling agent and/or a polymer matrix. Having a compound material allows to have other properties, in particular such as to enable die-casting, or injection or blow-moulding or other production techniques. Pure desiccant materials often have properties that do not allow such production, and therefore combining with one or more other materials greatly expands such possibilities. The compound material as a whole will still have desiccant properties, and may therefore also be called a desiccant.

Having the supply reel substantially made of desiccant further improves the moisture absorption characteristics, in that it provides a relatively large volume of desiccant material inside the housing, or even inside the subhousing, as the case may be. Since a substantive part of the volume is now a desiccant, there is ample absorption capacity as well as (still) a small volume to keep dry.

In embodiments, the collecting reel at a surface thereof comprises a desiccant. After using reagent and analysing same, its further fate is irrelevant. Yet, the volume of liquid absorbed by the reagent might, and in fact often will, eventually end up in the air in the housing. This added moisture may affect unused reagent, in that that unused reagent may absorb this added moisture from the air inside the housing. By providing desiccant also on the collecting reel, an even larger total surface area in the housing is provided with desiccant. In particular, the collecting reel is substantially made of desiccant, that is, the collecting reel is made for at least 50%, preferably at least 90%, and more preferably of 100% from desiccant material. This enhances the moisture absorption capabilities even further. The desiccant material may be the same, similar to, or different than the desiccant material at the surface of the supply reel.

In embodiments, the desiccant of the supply reel and/or of the collecting reel is or comprises a molecular sieve, such as activated carbon or a silica. In particular, the desiccant is a compound material as described above, made up of at least a pure desiccant material, such as silica or clay, a channeling agent such as ethylene-vinyl alcohol (EVOH) or polyvinyl alcohol (POH), and a polymer such as polythene or polypropylene. Reference is explicitly made to document U.S. Pat. No. 5,911,937 to Capitol Specialty Plastics, Inc., that discloses a number of useful components and methods to produce same. Said company also marketed the moisture absorbing Activ-Vial™ series with the proprietary M3003. Such substances and technologies may be used in the present invention. Yet, other pure desiccant, such as anhydrated salts or the like, may also be used.

In the above, "substantially made of" means that the collecting reel is made for at least 50%, preferably at least 90%, from desiccant (in particular compound) material. Thus, to be precise, the compound material, which need not be homogeneous or even a chemically bonded material, may form up to 100% of the material of the supply reel. The true and pure desiccant material, such as silica or clay, will be present in a lower percentage, in order to maintain in particular the desired properties of the polymer. Advantageous percentages are around 50%, and depend on the type of polymer used. Yet, other percentages may still provide good absorption properties. And besides the true desiccant material, the polymer and the channeling agent, other substances may also be provided, e.g. as disclosed in the cited patent document.

It is furthermore noted that a particular advantage of these embodiments resides in the fact that the desiccant is present in a large amount but not all at the surface, and rather embedded in the matrix of the reel(s), reachable via the channels as provided by the channeling agent during the production process. This ensures that the total moisture absorption capacity is rather high. But it also ensures that any time the housing is opened, and the contents, in particular the reagent pads, are exposed to the moisture of the environment, the desiccant is not totally flooded with moisture. Rather, the speed with which moisture is absorbed by the material is lower than could be if all the desiccant were provided at the surface. But that is not a problem, but rather an advantage. For it does not make sense to have the desiccant absorb much more moisture than would have been absorbed by the (unused) reagents, by more or less trying to desiccate all of the environment. It suffices in this case that the desiccant would absorb the moisture as much as possible only after reclosing of the housing. And that is exactly what happens with the provided reel(s): it has (they have) a high moisture absorption capacity but a low moisture absorption speed. Of course, for particular purposes it may still be advantageous if the moisture absorption speed is (very) high, in which case it would be possible to provide all or most of the true desiccant at or near the surface of the reel(s) and possibly other parts.

It is pointed out that in particular the embodiments (though not only these) wherein both reels are made of a material that itself comprises desiccant, when combined with the embodiments with a subhousing for the supply reel, provide an excellent useful life. As a first measure (of course besides closing off the housing as well as possible), moisture is absorbed by the desiccant material at or of the collecting reel itself, which may be a substantive amount. All this helps to keep the moisture level inside the housing at a low level. It is only from this environment within the housing that moisture may leak further into the subhousing with the supply reel, which represent the third measure. Second, the little moisture that can seep into the subhousing is effectively absorbed by the desiccant at or of the supply reel. All these measures together have ensured an effective useful life for tested systems, even in a hostile barn environment, of at least 6 months. This is particularly useful for reagents for tests that need not be performed at every milking. For example tests relating to the reproductive cycle, such as measuring a progesteron level, need only be performed during, say, a few days per year per dairy animal. It is then very advantageous if the analysis system still provides reliable results after a possibly very long time, without human intervention. Other tests, such as for milk components such as BHB (beta-hydroxybutyrate) or MUN (milk urea nitrogen) may be applied more often.

An additional advantage may be obtained if further parts of the sampling unit is provided with desiccant material, such as the housing itself, that may be lined with (pure or compound) desiccant material. For this, the same or similar material may be used. It is also possible to line e.g. the inner side of the housing with more or less pure desiccant material or cover it with liner made of a same or similar material as used for the tape reel(s).

Figure 2:
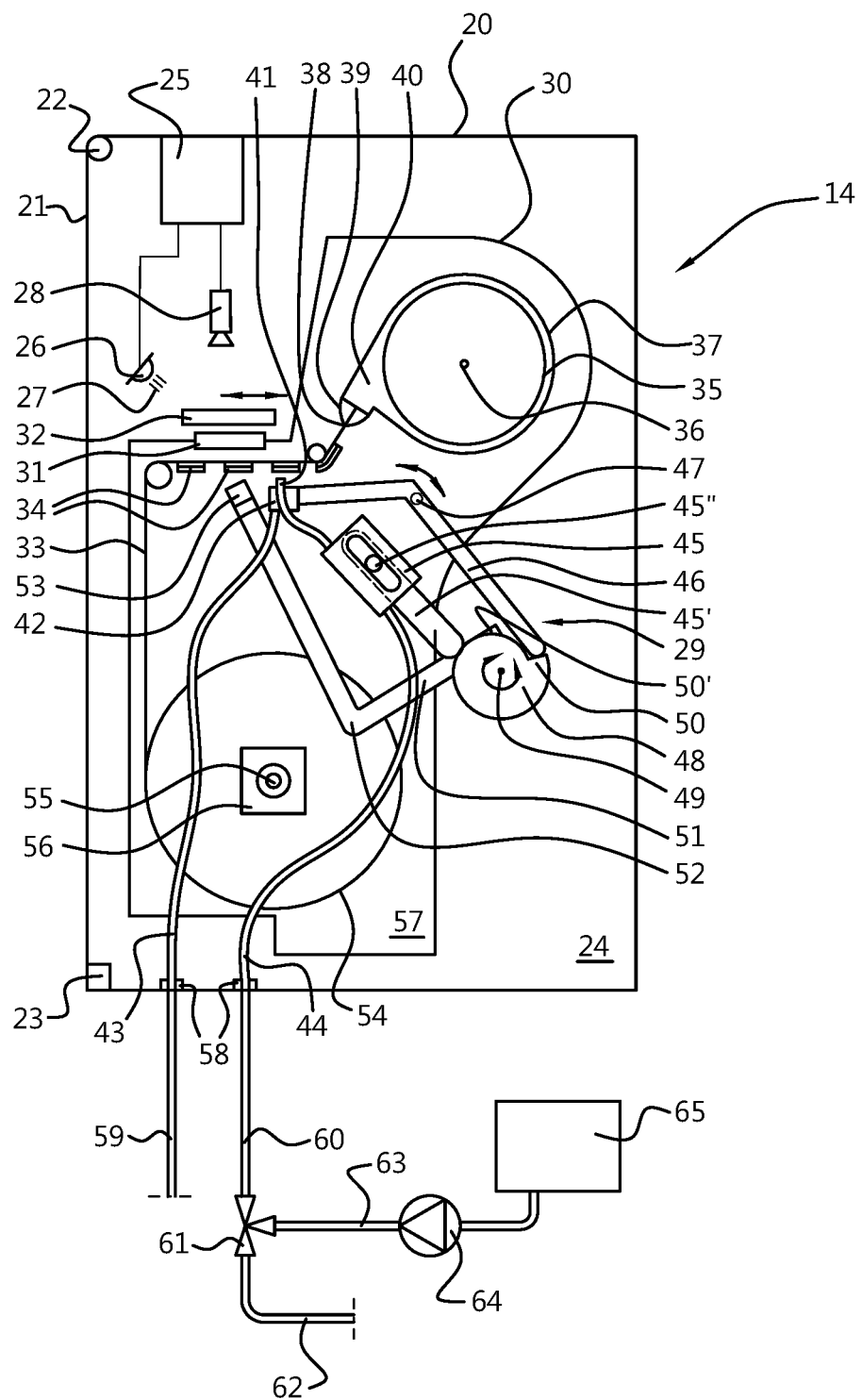

The invention will now be explained further by means of a number of embodiments described below and in the drawings, in which:

FIG. 1 shows a diagrammatic representation of a milking system according to the present invention; and FIG. 2 shows a diagrammatic representation of a sampling unit as in the milking system according to the present invention.

FIG. 1 shows a diagrammatic representation of a milking system 1 according to the present invention for milking teats 101 of an udder 100 of a dairy animal. The milking system 1 comprises teat cups 2, connected to short milk lines 3, debouching in a milk jar 4, that in turn is connected to a main milk line 5. A milk pump is denoted 6, and a three-way valve with 7 connects to a bulk tank line 8 connected to a bulk milk tank 9, and to a sewer line 10.

A milking robot 11 has a robot arm 12 and a robot control unit 13. A sampling unit is generally denoted 14, and a sampling line 15 with an optional sample valve 16.

In use of the milking system 1, the robot control unit 13 controls the milking robot 11 with the robot arm 12 to attach the teat cups 2 to the teats 101 of the udder 100 of a dairy animal such as a cow. The milk that is subsequently milked leaves the teat cups 2 under the influence of a vacuum, that is applied by a pump not depicted here, via the short milk lines 3, and is collected in a milk jar 4.

In order to comply with legal requirements, the first milk from each teat must be tested for physical changes, and if desired for other deviant properties. This can be done by means of a separate foremilk test device, or it can be done with the help of the sampling unit 14 as supplied according to the invention. Then use will be made of the alternative sample lines 15'. In case of a negative assessment, the milked milk collected in the milk jar 4 will then be pumped to the sewer line 10 by means of the milk pump 6, via the main milk line 5 and the three way valve 7. All these devices are under the control of the robot control unit 13. Contrarily, if the milk is assessed to be OK, it will be pumped to the bulk milk tank 9 via the bulk line 8.

It is also possible that the sampling unit 14 takes a sample from the milk jar 4, in particular a mixed sample from milk that was milked from all teats and during all of the milking. This helps to get a good assessment of the milk that (if not rejected based on the foremilk assessment or otherwise, such as being antibiotics milk) will be sent to the bulk tank 9, or possible to one of several bulk milk tanks. For example, the milk from different cows could be sent to different bulk tanks, based on their fat content, their protein content or otherwise, as determined by the sampling unit 14. In such embodiments, as the one shown in FIG. 1, the sample line 15 runs from the milk jar 4 to the sampling unit 14, and optionally has a sample valve 15. Note that the latter could also be a part internal to the sampling unit 14.

Most often, however, the sampling unit 14 is used to determine a property of the milk from a cow, either per teat quarter 101 or for the whole udder 100/animal, which property is subsequently used in animal management but not for immediate control of the milk destiny. Examples are the measurement of hormones such as progesterone, that play a role in the reproductive cycle of the animal, or of substances that relate to feeding or metabolic health of the animal.

Based on the assessment by the sampling unit 14, the farmer or the control unit 13 may then adapt feeding, call a veterinary for a health check or for insemination, and so on.

FIG. 2 shows a diagrammatic representation of a sampling unit 14 as in the milking system according to the present invention. The sampling unit 14 has a box 20 with a lid 21 that hinges around a hinge 22 and is locked with a lock 23, and with an in-box space 24. In the box 20 there are provided a sampler control unit 25, a light source 26 emitting light 27, a camera 28, a drive 29 and a cassette 30.

The cassette 30 has a window 31, that can be covered with a shutter 32, and through which a tape 33 with reagent pads 34 may be observed. The tape 33 is wound from a supply reel 35, rotatable around an axle 36 in a subhousing 37, that has an exit opening 38 closed by means of a seal 39 and that surrounds an internal subhousing space 40. A nozzle is denoted by 41, is partly surrounded by an overflow cup 42 with a housing drain line 43, and is itself connected to a housing supply line 44, which is controlled by a sample pump 45.

The drive 29 comprises a nozzle mover arm 46, which is hingeably driveable around a hinge 47 by a first cam wheel 48, which in turn is rotatably driven around an axle 49 by non-shown cam wheel drive and which has a first cam 50. The drive 29 also comprises a pump drive arm 45', which drives a moveable pump element 45". The drive 29 also comprises an rinsing cup mover arm 51 that is driveable around a hinge 52 by a second cam 50', and that at its end carries a rinsing cup 53.

The used tape is collected around a collecting reel 54 that is driveable around an axle 55 by means of a tape drive 56. The inner housing space is denoted by 57. Liquid connectors 58 supply connections for an external drain line 59 and an external supply line 60, the latter being connectible, via valve device 61, to a milk sampling line 62, such as the sampling line 15 of FIG. 1, as well as a cleaning fluid supply line 63, that supplies cleaning fluid via a supply pump 64 from a reservoir 65.

The sampling unit 14 as shown here comprises a substantially light- and airtight box 20, with a number of fixed parts and a replaceable cassette, or housing, 30 with a relatively large number of parts that are replaced each time the cassette 30 is replaced. However, it is e.g. also possible to limit the replacement to the supply reel 35 with the tape 33 with the reagent pads 34. This will be shown later on.

In the embodiment of FIG. 2, the cassette or housing 30 may be exchanged by unlocking the lock 23, such as by turning a key, shifting a bolt or the like, subsequently opening the lid 21 around the hinge 22, taking out the used cassette 30 and replacing it with a new and unused cassette. The fluid connections 58 between housing drain line 43 and the external drain line 59, and between the housing supply line 44 and the external supply line 60, respectively are made, either manually or automatically by placing the cassette 30. The various arms 45', 46, 51 driveable by the drive 29 are in an idle position in which they come to rest against respective cams, two of which are shown here as the first and second cams 50, 50', respectively. Thereafter the sampling unit 14 is closed again.

In use, a sample of milk is supplied through the milk sampling line 62, such as from the milk jar 4 in FIG. 1, and via the valve device 61 and the external supply line 60, a fluid connector 58, the housing supply line 44 the sample pump 45 and the nozzle 41. Thereto, the sample pump is put in an open position by means of the moveable pump element 45", driven by the pump drive arm 45' under the control of the drive 29, in turn controlled by the sampler control unit 25. It is noted that the sampler control unit is a part inside the box 20, and separate from the robot control unit 13 in FIG. 1. It is also possible that the sampler control unit is provided outside the box 20, still as a separate part, or even as an integral part of the robot control unit 13. The sample pump 45 may be any suitable pump such as a peristaltic pump. The latter has an advantage in that it is easily closable, such as by pressing the moveable pump element against an abutment surface, and is accurately controllable for dosing small amounts, such as a droplet of sample onto a reagent pad. Nevertheless, other types of pumps that can provide good dosing control are not excluded.

A droplet of the sample is thus provided by the nozzle 41 on a reagent pad 34. These reagent pads 34 are provided as a series of consecutive pads on a tape 33, and provide a detectable response in the presence of a (detectable) amount of to-be-detected substance in the milk sample. For example, the reagent pad 34 may show a colouring in the presence of progesterone in the milk sample, the intensity of speed of the colouring depending on the concentration of the progesterone. of course, other substances may also be used. The response, or absence thereof, is detected by means of a camera 28 that images, through a window 31 in the box, radiation coming from the reagent pads 34. This radiation is either radiation 27 that was emitted by the light source 26, and then reflected or scattered by the reagent pad 34, or may be radiation of a different type, generated by a reaction in the reagent to the radiation 27 from the light source 26, such as a fluorescence reaction. The light source 26 may emit optical radiation, such as visible light, UV(A) radiation or (near) infrared light, and is selected suitable, such as from corresponding LEDs or other. The window may optionally be covered by means of a shutter 32 that is movable in the direction of the double arrow, in order to protect the contents of the cassette 30, and in particular the tape 33 with the reagent pads 34, against any negative influences of the radiation.

After the nozzle 41 supplies a droplet of the milk sample to a reagent pad 34, the camera 28 observes the pad, and detects any response. Thereto, the pad 34 is first moved by means of the tape mover 56 that pulls the tape 33 a bit forward. This not only frees up a subsequent pad 34, but also moves the pad to the field of view of the camera 28. Note that it is also possible that that field of view is where the sample droplet is provided by the nozzle 41. that allows the new unused pad to stay in a protected environment for as long as possible. Preferably, the field of view of the camera 28 contains more than one reagent pad 34. This allows a reagent pad to stay in view for more than the average milking/sampling time. For dairy cows and sampling every cow, this time may be as short as a few minutes. Such a short time requires a relatively high dose of reagent in the reagent pads. This is not necessary if the reagent pad stays in view for a longer time, such as double or triple the time, which can be achieved by having two or three reagent pads in view of the camera 28. Of course, other numbers are possible as well, although very high numbers reduce the amount of visual information that the camera 28 may extract from each individual reagent pad 34.

After assessment by the camera 28, the tape 33 with the now used reagent pads is pulled further forward by the tape mover 56, and is eventually wound onto the collecting reel 54. The tape mover 56 may be any kind of motor for turning the collecting reel 54, such as a motor from a cassette deck, or a stepper motor.

A tape 33 may comprise more than one type of reagent pad 34. The reagents for such reactions are often enzymes or other biologically active substances. Very often, these are quite sensitive to moisture, that can affect their properties. For example, moisture alone may lead to a colour reaction, which is of course undesirable because it is meaningless. It may also lead to a different sensitivity of the reagent, which deteriorates the accuracy of the measurement. For these and other reasons, it is advantageous that the presence of moisture is prevented and suppressed as much as possible.

The present invention suppresses moisture by a number of possible measures. First of all, and obviously, the box 20 is made as airtight as possible, so that moisture may in principle only be provided by air in the in-box space 24, the volume of which can be kept small. It is furthermore possible to provide moisture absorption inside the box 20, such as by means of an absorptive lining or by means of packages of absorbers such as silica gel or the like. However, because the box 20 is in Principe a permanent part of the sampling unit of the milking system, such liners will inevitable become moisture saturated and thus ineffective, while the same holds for the absorber packages, that in the end will need replacement, which represents an undesirable human intervention if it can be prevented.

The cassette 30 in which the tape is provided need never have a higher (relative) humidity than the in-box space 24. Nevertheless, some moisture may seep through the box wall, because there will always be connections, either permanent or temporary. But more importantly, sampling inherently brings moisture into the cassette 30. Thus, measures to suppress moisture inside the cassette 30 are desirable as well. Thereto, for example, the supply reel 35 with the part of the tape 33 with unused reagent pads 34 is provided in a subhousing 37. The tape 32 exits the subhousing via an exit opening 38 that is sealed by means of e.g. a duckbill seal 39 or other suitable seal. This ensures that moisture from the inner housing space 57 will only very slowly enter the internal subhousing space 40. Since the tape 33 with the reagent pads 34 can, and will, be produced in a very dry environment, the air in the subhousing 37 can have an extremely low (relative) humidity of, say, only a few %. Depending on the quality of the duckbill, the low humidity need rise only very slowly.

In order to further suppress moisture, the supply reel 35 itself is provided, according to the invention, at least at its surface with a desiccant. In the presently shown example, the supply reel 35 is substantially made of a material with desiccant properties, which means that it is able to actively remove water from the surrounding air. This further ensures that the humidity inside the subhousing 37, thus at the unused reagent pads 34, remains at a suitable level, such as a few %, for an even longer time. And since the supply reel 35 may take up a substantial volume within the subhousing 37, depending on the ratio between the fully wound tape and the diameter of the supply reel 35, the total moisture absorption capacity may be very high.

The moisture absorption properties depend on the material used. Preferably, the material is a compound material, comprising at least a true deiccant/moisture absorber/adsorber, and a matrix to provide sufficient strength to the supply reel 35. A useful example is marketed by the company Capitol Specialty Plastics, Inc., for example for its Active-Vial™ M3003 series. Such materials comprise a physical desiccant, in which moisture is collected in microscopic pores (microsieve), surrounded by a polymer matrix, such as from polypropylene, polyethylene, mixtures thereof, and so on. To this is added a so-called channeling agent, such as EVOH (ethylene-vinyl alcohol), that ensures that channels are formed during (actually: after) mixing of the desiccant material and the (molten) polymer. These channels ensure that moisture can reach the desiccant material that was embedded in the polymer matrix. Thus, even deep-lying desiccant material can attract and bind moisture from the air, which greatly enhances the total absorption capacity. Yet, it is also possible to have the (true) desiccant material mainly at the surface of the supply reel 35. For example, in cases where the supply reel 35 is used for a relatively short time only, it may be better to have a high speed of absorption, with less total absorption capacity.

Yet a further optional measure is to have the collecting reel 54 also comprise desiccant material at least at its surface. Optionally, the collecting reel 54 is also substantially made of desiccant material, in much the same way as described above for the supply reel 35. the advantages are manifold, e.g. in that all moisture in the air in the the inner housing space 57, in particular from supplied samples that escapes to the inner housing space 57, may be absorbed by the collecting reel 54. This helps reduce the humidity in said space, which in turn limits the seeping of moisture to the subhousing 37. Note that providing such a subhousing 37 is not necessary, although advantageous, especially if the collecting reel 54 is also provided with, or from, desiccant material, since then there is a very large moisture absorption capacity and/or speed from both reels 35 and 54.

The above described embodiments only serve to help explain the invention without limiting this in any way. The scope of the invention is rather determined by the appended claims.

The invention claimed is:

1. A milking system, comprising
a milking device;
at least one milk line for carrying milk from the milking device; and
a sampling unit that is arranged to take a sample from the milk line and to test the sample for the presence or concentration of at least one substance,
wherein the sampling unit is provided with a control unit and a housing, wherein the housing comprises therein a supply reel with a tape that carries a reagent, and a sample supplier to supply, under control of the control unit, at least a part of the sample to the reagent on the tape,
the sampling unit further comprising a tape displacer displacing the tape under control of the control unit, a sample analyser, and a used tape collector device collecting tape with reagent to which a sample has been supplied,
wherein the supply reel at a surface thereof comprises a desiccant.

2. The milking system according to claim 1, wherein the used tape collector device is provided in the housing.

3. The milking system according to claim 2, wherein the supply reel is provided in a subhousing within the housing with an exit opening for the tape.

4. The milking system according to claim 2, wherein the used tape collector device comprises a collecting reel onto which the tape with the used reagent is collected by the tape displacer.

5. The milking system according to claim 2, wherein the supply reel at a surface thereof comprises a desiccant made of a mixed material, comprising a desiccant, a channeling agent and a polymer.

6. The milking system according to claim 1, wherein the supply reel is provided in a subhousing within the housing with an exit opening for the tape.

7. The milking system according to claim 6, wherein the used tape collector device comprises a collecting reel onto which the tape with the used reagent is collected by the tape displacer.

8. The milking system according to claim 6, wherein the supply reel at a surface thereof comprises a desiccant made of a mixed material, comprising a desiccant, a channeling agent and a polymer.

9. The milking system according to claim 1, wherein the used tape collector device comprises a collecting reel onto which the tape with the used reagent is collected by the tape displacer.

10. The milking system according to claim 9, wherein the used tape collector device is provided directly in the housing.

11. The milking system according to claim 9, wherein the collecting reel at a surface thereof comprises a desiccant.

12. The milking system according to claim 9, wherein the supply reel at a surface thereof comprises a desiccant made of a mixed material, comprising a desiccant, a channeling agent and a polymer.

13. The milking system according to claim 9, wherein the collecting reel is made of is made of a mixed material that contains a pure desiccant, and at least one other material.

14. The milking system of claim 13, wherein the at least one other material is selected from a binder, a channeling agent and a polymer matrix.

15. The milking system according to claim 9, wherein the desiccant of the supply reel and/or of the collecting reel is or comprises a molecular sieve.

16. The milking system according to claim 9, wherein the supply reel and/or the collecting reel is a die cast part, a blow-moulded part or an injection moulded part.

17. The milking system according to claim 15, wherein the molecular sieve is a silica or an activated carbon.

18. The milking system according to claim 1, wherein the supply reel is made of a mixed material that contains a pure desiccant, and at least one other material.

19. The milking system of claim 18, wherein the at least one other material is selected from a binder, a channeling agent and a polymer matrix.

* * * * *